(12) United States Patent
Mensch et al.

(10) Patent No.: US 11,771,328 B2
(45) Date of Patent: Oct. 3, 2023

(54) CORE TEMPERATURE SENSOR WITH THERMAL CONDUCTIVITY COMPENSATION

(71) Applicants: Robert Bosch GmbH, Stuttgart (DE); Beatrix Mensch, Illertissen (DE); Thomas Rocznik, Mountain View, CA (US); Christian Peters, Sunnyvale, CA (US); Seow Yuen Yee, Mountain View, CA (US)

(72) Inventors: Beatrix Mensch, Illertissen (DE); Thomas Rocznik, Mountain View, CA (US); Christian Peters, Sunnyvale, CA (US); Seow Yuen Yee, Mountain View, CA (US)

(73) Assignee: Robert Bosch GmbH, Stuttgart (DE)

( * ) Notice: Subject to any disclaimer, the term of this patent is extended or adjusted under 35 U.S.C. 154(b) by 308 days.

(21) Appl. No.: 16/761,841

(22) PCT Filed: Dec. 21, 2018

(86) PCT No.: PCT/US2018/067005
§ 371 (c)(1),
(2) Date: May 6, 2020

(87) PCT Pub. No.: WO2019/126607
PCT Pub. Date: Jun. 27, 2019

(65) Prior Publication Data
US 2021/0196128 A1 Jul. 1, 2021

Related U.S. Application Data

(60) Provisional application No. 62/609,989, filed on Dec. 22, 2017.

(51) Int. Cl.
*A61B 5/01* (2006.01)
*G01K 13/20* (2021.01)
(Continued)

(52) U.S. Cl.
CPC .............. *A61B 5/01* (2013.01); *A61B 5/742* (2013.01); *G01K 1/165* (2013.01); *G01K 7/16* (2013.01);
(Continued)

(58) Field of Classification Search
None
See application file for complete search history.

(56) References Cited

U.S. PATENT DOCUMENTS 4,465,077 A * 8/1984 Schneider ................ G01K 7/24
706/924
9,015,001 B2 * 4/2015 Shimizu ................ G01K 13/20
702/131

(Continued)

OTHER PUBLICATIONS

International Search Report and Written Opinion corresponding to PCT Application No. PCT/US2018/067005, dated Apr. 17, 2019 (12 pages).

(Continued)

*Primary Examiner* — Benjamin S Melhus
(74) *Attorney, Agent, or Firm* — Maginot, Moore & Beck LLP

(57) ABSTRACT

In one embodiment, a temperature sensor system includes a sensor assembly with a temperature sensing portion configured to generate a first signal based upon a temperature of body proximate a surface portion of the temperature sensing portion, and a thermoelectric generator portion configured to receive heat flow from the body through the temperature sensing portion and to generate a second signal based upon the heat flow. A control unit is operably connected to the sensor assembly and a memory and configured to execute program instructions stored in the memory to calculate and output a corrected temperature based upon the first signal, the second signal, and at least one correction factor stored in the memory. The at least one correcting factor is determined (Continued)

based upon at least one of a thermal conductivity of the sensor assembly, a size of the sensor assembly, and an aspect ratio of the sensor assembly.

10 Claims, 6 Drawing Sheets

(51) Int. Cl.
    *G01K 1/16*     (2006.01)
    *G01K 7/16*     (2006.01)
    *A61B 5/00*     (2006.01)
    *G01K 15/00*     (2006.01)

(52) U.S. Cl.
    CPC ........... *G01K 13/20* (2021.01); *G01K 15/005* (2013.01); *A61B 2562/0271* (2013.01)

(56) References Cited

U.S. PATENT DOCUMENTS

| | | | | |
|---|---|---|---|---|
| 9,528,887 | B2* | 12/2016 | Shimizu | G01K 7/42 |
| 10,750,951 | B1* | 8/2020 | Prachar | G01K 13/20 |
| 2006/0056487 | A1* | 3/2006 | Kuroda | G01K 1/165 |
| | | | | 374/E7.042 |
| 2007/0295713 | A1* | 12/2007 | Carlton-Foss | G01K 1/16 |
| | | | | 219/497 |
| 2012/0109571 | A1 | 5/2012 | Shimizu | |
| 2012/0143079 | A1* | 6/2012 | Lia | A61B 5/14552 |
| | | | | 600/549 |
| 2012/0289855 | A1 | 11/2012 | Bieberich et al. | |
| 2014/0221796 | A1 | 8/2014 | Lia et al. | |
| 2016/0169704 | A1 | 6/2016 | Badeja et al. | |
| 2017/0049397 | A1* | 2/2017 | Sun | G01K 7/427 |
| 2017/0100042 | A1 | 4/2017 | Shrubsole et al. | |
| 2018/0008149 | A1* | 1/2018 | Pekander | G01K 7/427 |
| 2018/0242850 | A1* | 8/2018 | Ellis | A61B 5/02007 |
| 2019/0142280 | A1* | 5/2019 | Bongers | A61B 5/0002 |
| | | | | 600/549 |

OTHER PUBLICATIONS

März, Martin et al., "Thermal modeling of power-electronic systems," Infineon Technologies AG, Munich, 2000 (20 pages).

* cited by examiner

CORE TEMPERATURE SENSOR WITH THERMAL CONDUCTIVITY COMPENSATION

This application is a 35 U.S.C. § 371 National Stage Application of PCT/US2018/067005, filed on Dec. 21, 2018, which claims the benefit of U.S. provisional patent application No. 62/609,989, filed on Dec. 22, 2017, the disclosures of which are incorporated herein by reference in their entirety.

FIELD

The device and method disclosed in this document relates to thermal sensing and, more particularly, to thermal sensing of core temperatures.

BACKGROUND

The core body temperature of a creature such as a human can be calculated using measurements from a sensor placed on the skin. The sensor measures the heat flux through the sensor and the skin temperature. The heat flux and temperature measurements are used in an equation to compute the core body temperature.

The equation used in the above calculation of core body temperature is based upon the assumption that the heat flow through the sensor only occurs perpendicular to the skin surface upon which the sensor is placed. Using this assumption, the heat flow through the sensor is considered to be the same as the heat flow through the skin. In reality, however, lateral heat flow also occurs within the sensor. Accordingly, the measurement of heat flux within the sensor that is perpendicular to the skin varies from the actual heat flow out of the skin.

By way of example, FIG. 1 is a schematic representation of a known sensor model 10 used to determine core body temperature when the sensor is placed on the skin of a body. In the model 10, the body core temperature ($T_C$) is modeled as a voltage source 12, the thermal resistance of the skin ($R_{th, skin}$) is modeled as a resistor 14, the thermal resistance of the sensor ($R_{th, sensor}$) is modeled as a resistor 16, the thermal resistance of the air layer ($R_{th, air}$) is modeled as a resistor 18, and the temperature of the ambient air is modeled as a voltage source 20.

As can be seen from FIG. 1, the difference between the temperature of the body core ($T_C$) and the outer surface of the skin ($T_s$) is thus a function of the thermal resistance of the skin ($R_{th, skin}$). Likewise, the difference between the temperature of the outer surface of the skin ($T_s$) and the outer surface of the sensor ($T_a$) is a function of the thermal resistance of the sensor ($R_{th, sensor}$) and the difference between the temperature of the outer surface of the sensor ($T_a$) and the air layer ($T_{amb}$) is a function of the thermal resistance of the air ($R_{th, air}$).

The thermal variables for the model of FIG. 1 are provided in the following table:

| Thermal | | | Electrical | | |
| --- | --- | --- | --- | --- | --- |
| Variable | Symbol | Unit | Variable | Symbol | Unit |
| Temperature | T | K | Voltage | V | V |
| Heat Transfer Rate | q | W | Current | I | A |
| Heat Flux | $\dot{Q}''$ | W/m² | Current density | J | A/m² |
| Thermal Resistance | $R_{th}$ | K/W | Resistance | R | Ω |
| Thermal Capacity | $C_{th}$ | Ws/K | Capacitance | C | As/V |

For the model of FIG. 1, the heat transfer rate (q) can be calculated using Ohm's Law as follows:

$$q = \frac{\Delta T}{R_{th}}$$

Therefore, the heat flux ($\dot{Q}''$) can be calculated using the following equation:

$$\dot{Q}'' = \frac{\Delta T}{R_{th} \cdot A}$$

For each material layer in the model, the thermal resistance can be calculated using the following equation:

$$R_{th} = \frac{\Delta x}{k \cdot A} = \frac{1}{h \cdot A}$$

Where:
"ΔT" is the temperature difference across the material layer; "Δx" is the thickness of the material layer in a direction perpendicular to the surface of the skin;
"k" is the thermal conductivity of the material layer;
"A" is the area of the material layer; and
"h" is the heat transfer coefficient of the material layer.

The thermal capacity can also be calculated with the material parameter. In instances wherein the system is in steady state, however, the thermal capacity may be omitted.

As noted above, the model of FIG. 1 includes three thermal resistances. In this model, the sensor measures the skin temperature $T_s$ and the heat flux $\dot{Q}''$ through the sensor. Thus, with the assumption that the heat flow through the skin and the sensor is only perpendicular to the skin surface, the heat flux through the skin equals the heat flux through the sensor. Moreover, the temperature difference through the skin layer (ΔT) can be calculated as:

$$\Delta T = T_C - T_S$$

Therefore, the core body temperature can be calculated using the following equation:

$$T_C = \frac{\dot{Q}''}{h_S} + T_S$$

As noted above, however, the assumption that heat flow occurs only vertically to the skin does not reflect reality. Accordingly, the above computation associated with the model of FIG. 1 introduces errors into the calculated $T_C$.

What is needed is a system and method for determining the core temperature of a creature or object which is more accurate than known systems and methods. It would be beneficial if a system and method for determining the core temperature of a creature or object accounted for the mismatch between nominal heat flow out of the skin of a body and heat flow through a sensor perpendicular to the skin when the sensor is positioned on the skin.

SUMMARY

The present disclosure is directed to a system and method to more accurately determine the heat flow through the outer skin of a body using a measured heat flow through a sensor assembly. The disclosed system and method incorporates a consideration of the size and the aspect ratio of the sensor assembly on the thermal conductivity of the sensor assembly since those values are necessary for a more precise calculation of the heat flow through the outer skin.

Rather than using the measured heat flux through a sensor assembly as the value of the heat flux through the outer skin, the present disclosure uses a calculated heat flux through the outer skin by applying a correcting factor to the measured heat flux through the sensor assembly. The disclosure thus compensates for the mismatch between the heat flow in the sensor assembly and the nominal heat flow through the skin. The correcting factor is parameterizable with the dimensions and thermal conductivity of the sensor assembly.

In one embodiment, a temperature sensor system includes a sensor assembly with a temperature sensing portion configured to generate a first signal based upon a temperature of body proximate a surface portion of the temperature sensing portion, and a thermoelectric generator portion configured to receive heat flow from the body through the temperature sensing portion and to generate a second signal based upon the heat flow. A control unit is operably connected to sensor assembly and a memory and configured to execute program instructions stored in the memory to calculate and output a corrected temperature based upon the first signal, the second signal, and at least one correction factor stored in the memory. The at least one correcting factor is determined based upon at least one of a thermal conductivity of the sensor assembly, a size of the sensor assembly, and an aspect ratio of the sensor assembly.

In one or more embodiments, the control unit is configured to calculate the corrected temperature by using the at least one correcting factor to correct the heat flow through the sensor assembly to more accurately identify heat flow through an outer skin of the body.

In one or more embodiments, the at least one correcting factor is determined based upon the thermal conductivity of the sensor assembly, the size of the sensor assembly, and the aspect ratio of the sensor assembly.

In one or more embodiments, the system further includes a display, and the control unit is operably connected to the display and configured to execute the program instructions to display the calculated corrected temperature with the display.

In one or more embodiments, the sensor assembly and control unit are housed by a housing configured to expose the sensor assembly to the body through a first side of the housing while the housing includes a window on a side of the housing opposite the first side which is configured to transfer the heat flow received by the thermoelectric generator portion out of the temperature sensor system.

In one or more embodiments, the temperature sensing portion substantially surrounds the thermoelectric generator portion except at the surface portion.

In one or more embodiments, the control unit is further configured to execute the program instructions to calculate a corrected temperature (Tc) based upon a thermal resistance of an outer skin of the body being measured.

In one embodiment, a method of providing a corrected temperature includes obtaining, using a control unit executing program instruction stored in a memory, a first signal from a temperature sensing portion of a sensor assembly, the first signal based upon a temperature of body proximate a surface portion of the temperature sensing portion. The method further includes obtaining, using the control unit, a second signal from a thermoelectric generator portion of the sensor assembly, the second signal based upon a heat flow received by the thermoelectric generator portion from the body through the temperature sensing portion. The method then calculates, with the control unit, a corrected temperature (Tc) based upon the obtained first signal, the obtained second signal, and at least one correcting factor (K) stored in a memory, the at least one correcting factor (K) determined based upon at least one of a thermal conductivity of the sensor assembly, a size of the sensor assembly, and an aspect ratio of the sensor assembly.

In one or more embodiments, calculating, with the control unit, a corrected temperature (Tc) includes calculating, with the control unit, a corrected temperature (Tc) based upon the following equation:

$$\dot{Q}''_{skin} = \frac{\dot{Q}''_{sensor}}{K}$$

wherein $\dot{Q}''_{skin}$ is heat flux through an outer skin of the body, and $\dot{Q}''_{sensor}$ is heat flux through the sensor assembly.

In one or more embodiments, a method includes determining the at least one correcting factor (K) is based upon the thermal conductivity of the sensor assembly, the size of the sensor assembly, and the aspect ratio of the sensor assembly.

In one or more embodiments, a method includes displaying, under the control of the control unit, the calculated corrected temperature on a display.

In one or more embodiments, a method includes exposing the sensor assembly to the body through a first side of a housing, wherein the control unit and sensor assembly are housed by the housing, and transferring the heat flow received by the thermoelectric generator portion out of the temperature sensor system through a window on a side of the housing opposite the first side.

In one or more embodiments, a method includes using a sensor assembly wherein the temperature sensing portion substantially surrounds the thermoelectric generator portion except at the surface portion.

In one or more embodiments, calculating, with the control unit, the corrected temperature (Tc) includes calculating the corrected temperature (Tc) based upon a thermal resistance of an outer skin of the body.

BRIEF DESCRIPTION OF THE DRAWINGS

The foregoing aspects and other features are explained in the following description, taken in connection with the accompanying drawings.

DETAILED DESCRIPTION

Figure 1:
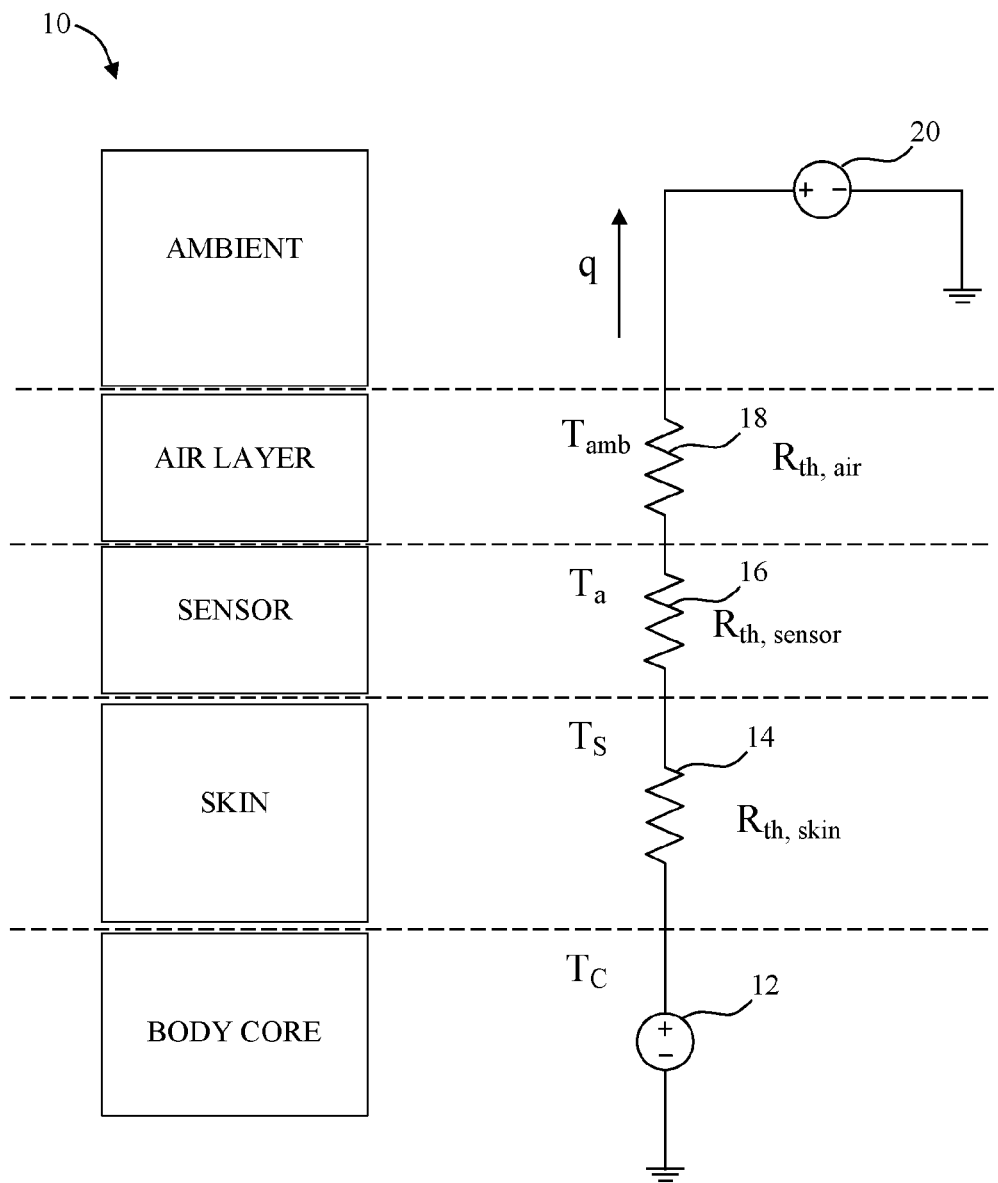
FIG. 1 is a schematic representation of a known sensor model used to determine core body temperature when the sensor is placed on the skin of a body.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art which this disclosure pertains.

Figure 2:
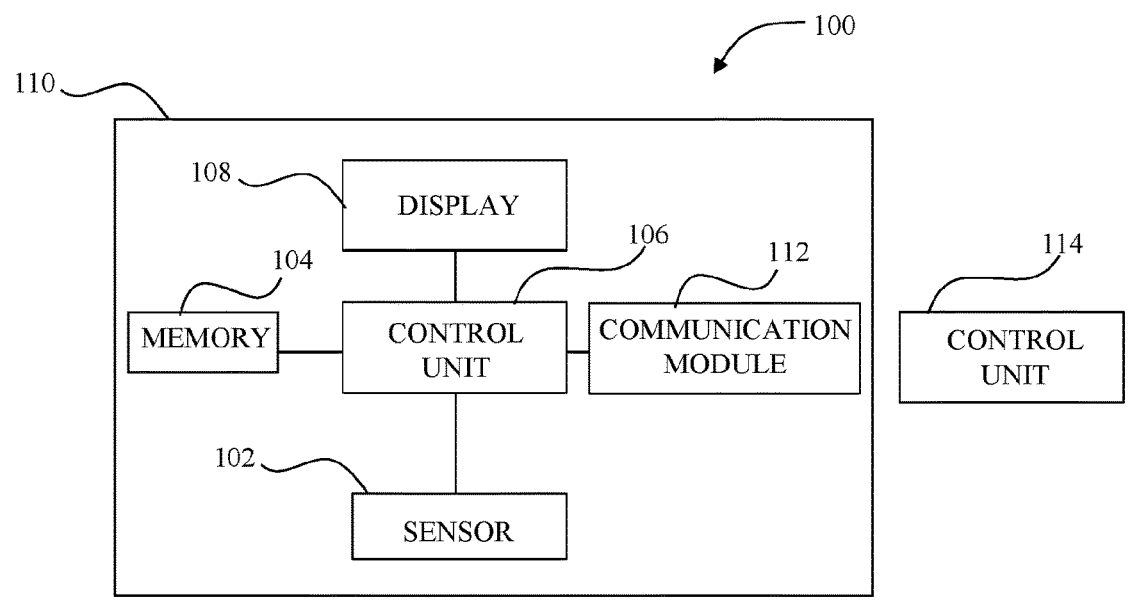
FIG. 2 shows a schematic view of a system which can be used to determine the core temperature of creatures or objects including a control unit that compensates for the mismatch between the heat flux measured by a sensor and the nominal heat flux through the skin.

FIG. 2 depicts a system 100 which includes a sensor assembly 102, a memory 104, a control unit 106, and an output device 108 which in one embodiment is a display. In some embodiments, one or more of the control unit 106 and the display 108 is located remotely from sensor assembly 102. In one embodiment, the sensor assembly 102 is supported by a housing 110.

Figure 3:
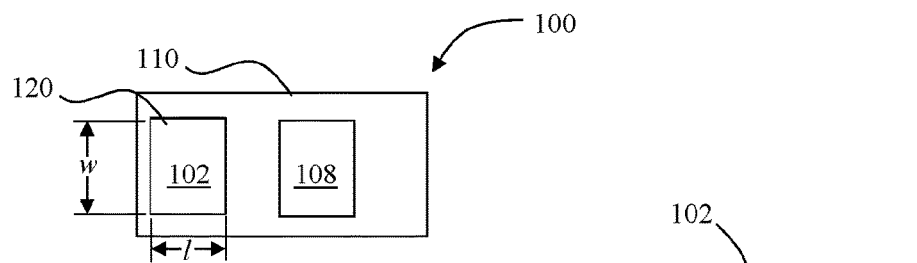
FIG. 3 depicts a top plan view of the system of FIG. 2.

While schematically depicted as within the housing 110 in FIG. 2, the sensor assembly 102 is positioned such that there is no impediment to heat flow through the upper or lower surfaces of the assembly 102. Thus, FIG. 3 depicts the system 100 with a window 120 which thermally exposes the upper surface of the sensor assembly 102. The window 120 in some embodiments is an opening in the housing 110 which directly exposes the upper surface of the sensor assembly 102 to ambient environment, clothing, or other surrounding. In other embodiments, the window 120 includes a material with a high thermal conductivity. In some embodiments, the lower surface of the sensor assembly 102 likewise includes a window 120.

The control unit 106 is operably connected to the sensor assembly 102 and the display 108. The control unit 106 is a control device which in different embodiments includes one or more integrated circuits (ICs), such as microcontrollers (small, complete computer systems, for example with its own processor and memory, which are formed as a single integrated circuit), application specific integrated circuits (ASIC), application-specific standard products (ASSP), and the like. The control unit 106 is configured to execute program instructions stored within the memory 104, which in some embodiments is a part of the control unit 106, to obtain signals from the sensor assembly 102, to determine the core temperature of creatures or objects using the obtained signals, and to control the display unit to display the determined core temperatures.

In some embodiments, the system 100 includes a communication module 112, in addition to or as an alternative to the display unit, which provides for external communication, either wired or wireless, of the obtained signals and/or the determined core temperatures. The communicated signals are then used by an external control unit 114 to determine the core temperature of a creature or object.

Figure 4:
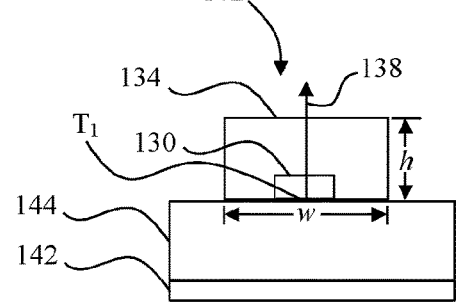
FIG. 4 depicts a side plan view of the sensor assembly of the system of FIG. 2.

The sensor assembly 102 is shown in schematic detail in FIG. 4. The sensor assembly 102 includes a temperature sensing portion 130 and a thermoelectric generator (TEG) portion 134 having a width (w) and a height (h) and length (l) (see FIG. 3). The temperature sensing portion 130 is configured so as to be positioned directly on the outer surface of the outer skin 144 of a creature or object and configured to provide signals to the control unit 106 representative of the core temperature 142 of the creature or object.

The temperature sensing portion 130 and the system 100 in general is further configured to minimize interference with transfer of heat through the sensor assembly 102. To this end, the TEG portion 134 in this embodiment substantially surrounds the temperature sensing portion 130 with the exception of the surface portion of the temperature sensing portion 130 which is configured to receive heat flow from a body. Some relatively small surfaces (not shown) which provide for electrical connection to the temperature sensing portion 130 may also not be covered by the TEG portion 134.

In some embodiments, the surface portion of the temperature sensing portion 130 contacting the body is protected by a material with high thermal conductance. Moreover, while FIG. 4 depicts a portion of the TEG 134 in physical contact with the body, in some embodiments the lower surface of the TEG 134 is spaced apart from the body by a thermally insulating layer. In any event, heat is transferred from an underlying substrate substantially directly through the temperature sensing portion 130 and then through the TEG portion 134 and out of the upper surface of the TEG portion 134 as indicated by the arrow 138.

The TEG 134 portion converts heat flux (temperature difference) directly into electrical energy through a phenomenon called the Seebeck effect (a form of thermoelectric effect). The TEG portion 134 in one embodiment is a solid state portion but can be any configuration which converts heat flux. The generated voltage in one embodiment is provided to the control unit 106. In other embodiments, a generated current is provided to the control unit 106.

While configured to the extent possible to mimic the nominal heat flow within the skin and obtain the nominal temperature of the outer surface of the skin, the sensor inherently modifies the heat flow and the temperature in the skin immediately adjacent to the sensor assembly. By way of example, FIG. 5 schematically represents an idealized scenario for a sensor assembly 150 and the idealized heat flow 152 directly perpendicular to the surface 154 of the skin and vertically through the sensor assembly 150.

Figure 5:
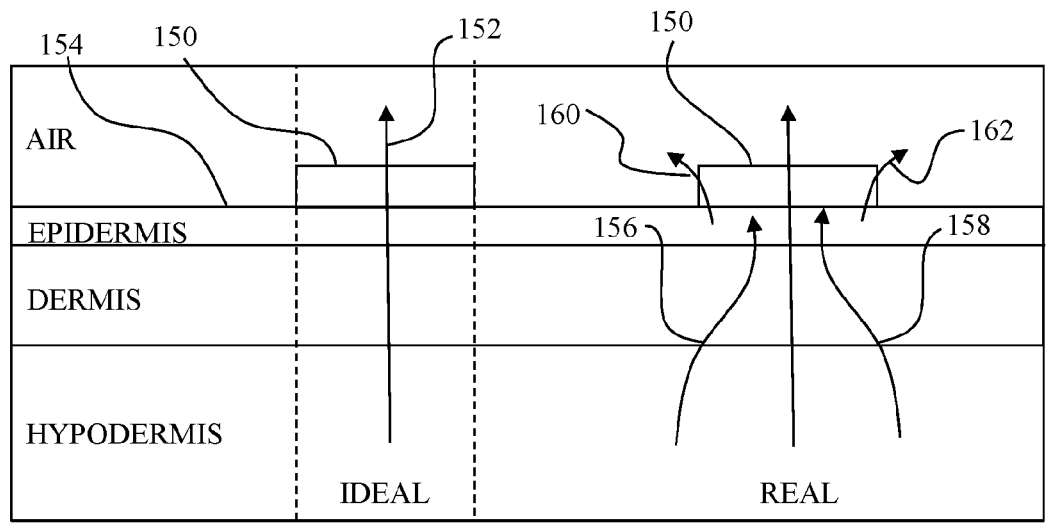
FIG. 5 depicts a schematic representation of heat flow through an ideal sensor and an actual sensor in which the thermal resistance of the sensor system is smaller than the resistance of the skin.

FIG. 5 also schematically depicts what actually occurs when the sensor assembly 150 is positioned on the skin of a body in a scenario wherein the sensor assembly 150 has a higher thermal conductivity than the air, while opposite behavior would occur in the case wherein the sensor exhibits a lower conductivity. Because the sensor assembly 150 in this embodiment has a higher thermal conductivity than the air, the heat emitted from the body is more attracted to flow through the sensor assembly 150 than though the air. Accordingly, heat which is initially moving perpendicularly through the skin is funneled toward the sensor assembly as indicated by the arrows 156 and 158. Accordingly, the temperature at the skin surface 154 beneath the sensor assembly 150 is actually higher than the nominal temperature at the surface of the skin. Additionally, the heat flow through the bottom surface of the sensor assembly 150 is higher than the nominal heat flow through the surface of the skin at a location which is not covered by the sensor assembly 150.

Moreover, all of the heat which enters the lower surface of the sensor assembly 150 (defined as the surface of the sensor assembly in contact with the surface of the skin or other body) does not flow out through the upper surface of the sensor assembly 150 (the surface of the sensor assembly opposite to the surface of the sensor assembly in contact with the skin). Rather, as indicated by the arrows 160 and 162, some of the heat flow moves non-vertically and escapes through the sides of the sensor assembly. Additionally, depending upon the housing and other components of the system, more or less heat may be directed toward the sensing assembly.

Because of the above described effects, the measured temperature and heat flux introduce errors into the calculation of the core body temperature. Accordingly, in the system 100, a correcting factor (K) which in one embodiment is stored within the memory 104 is applied by the control system 106 when executing the program instructions, whereby the actual heat flux through the skin is more accurately determined. In some embodiments, the correcting factor (K), which describes how much higher/lower the heat flow through the sensor assembly is than the nominal heat flow through the skin, is a stored value/function accessible by the control system 106 such as in the memory 104 of the control unit 106. The correcting factor is defined by the following equation:

$$K = \frac{q_{sensor}}{q_{skin}} = \frac{\dot{Q}''_{sensor}}{\dot{Q}''_{skin}}$$

For a particular system, the value/function of the correcting factor (K) is determined using a simulation tool such as the physics simulation tool FLUENT commercially available from Ansys, Inc. of Canonsburg, Pa. The predominant factors in determining the value/function of the correcting factor (K) for a particular system are the thermal conductivity of the sensor assembly material and the body, the size of the sensor assembly, and the aspect ratio of the sensor assembly.

To validate the effectiveness of the incorporation of the correcting factor (K), a two dimensional simulation was used to generate a correcting factor (K). The behavior of the system is the same as in three dimensions, but the absolute values are not the same. Thus, while performing the analysis in two dimensions is valid to show the principle of this method, three dimensional simulations provide more precise values and are typically used in the system 100.

In the simulation, three cases were analyzed. In each case, only one of the three variables (thermal conductivities (k), size (width (w) times height (h)), and aspect ratio (w/h) was varied. The same reference values $k_{ref}$, $w_{ref}$ and $h_{ref}$ are used in all three simulations. Due to the two dimensional simulation, the sensor assembly length (l) is not shown. A three dimensional simulation, however, would include the sensor assembly length (l) as well. For all three cases and for each simulation point the correcting factor K is calculated using the equation above.

Figure 6:
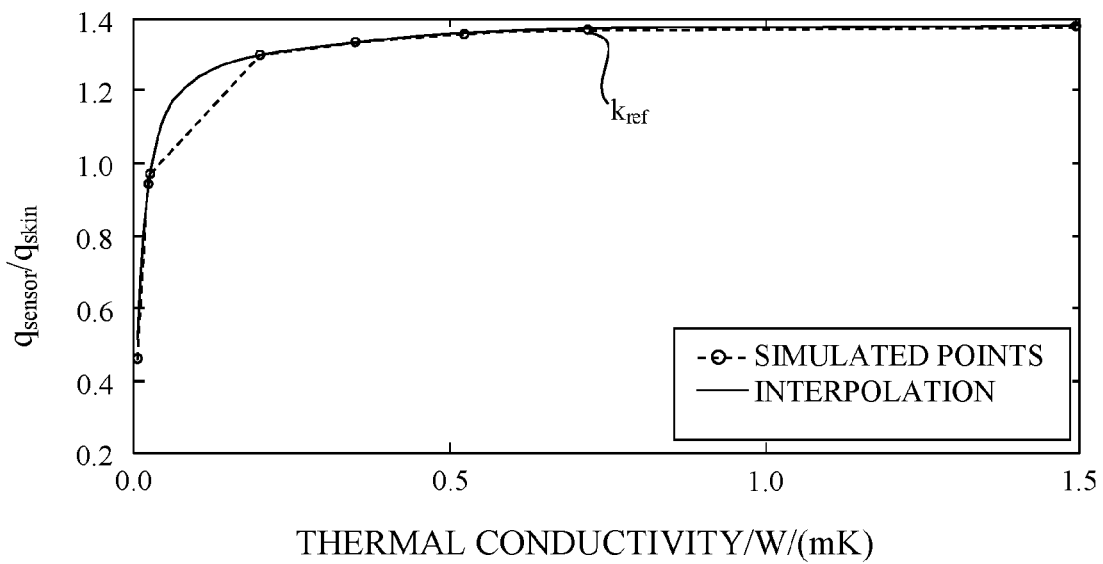
FIGS. 6-8 depict the results of simulations which establish a relationship between correcting factors and a sensor assembly's thermal conductivity, size, and aspect ratio.
Figure 7:
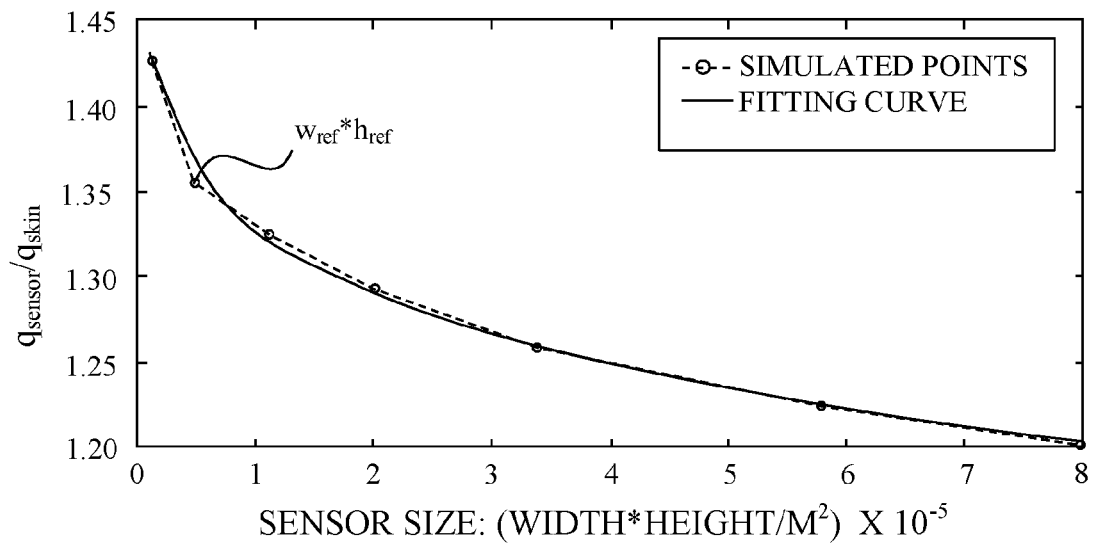
Figure 8:
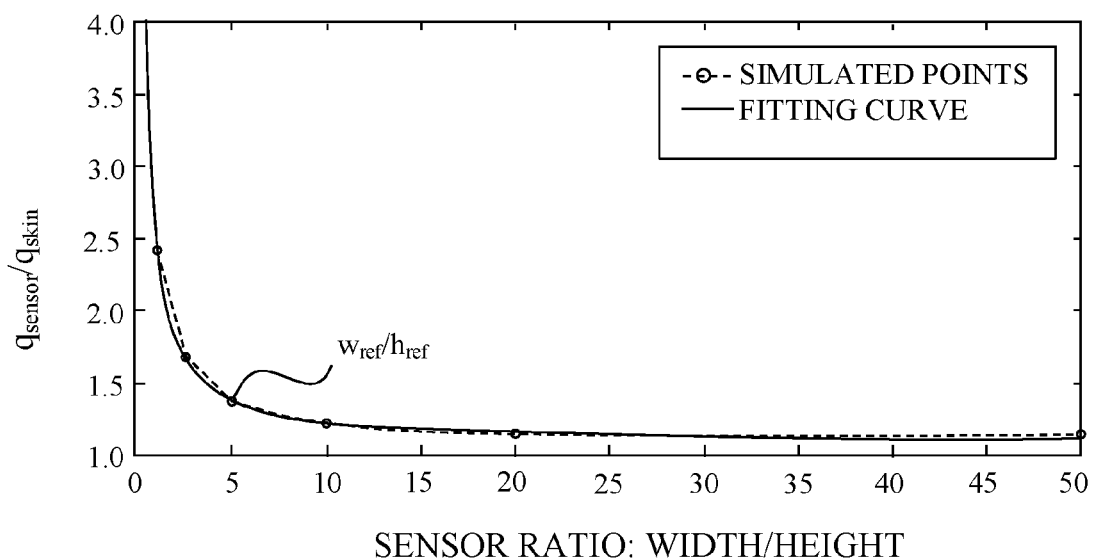

The results of the simulations are displayed in FIGS. 6-8. For each case the factor K is plotted against the value which is changed. For each case an interpolation is determined, so that the factors can be described with:

$$K_k = f_k\{k\}$$

$$K_{size} = f_{size}\{w,h\}$$

$$K_{ratio} = f_{ratio}\{w,h\}$$

With reference to FIG. 6, the size and aspect ratio were held constant at the $w_{ref}*h_{ref}$ value and $w_{ref}/h_{ref}$ value while the thermal conductivity of the sensor assembly was varied from the $k_{ref}$. In FIG. 7, the thermal conductivity of the sensor assembly was maintained at the $k_{ref}$ and the aspect ratio was maintained at the $w_{ref}/h_{ref}$ value while the size was varied from the $w_{ref}*h_{ref}$ value. In FIG. 8, the thermal conductivity of the sensor assembly was maintained at the $k_{ref}$ and the size was maintained at the $w_{ref}*h_{ref}$ value while the aspect ratio was varied from the $w_{ref}/h_{ref}$ value.

With the reference values from the above simulations, a reference factor $K_{ref}$ was calculated:

$$K_{ref} = f_k\{k_{ref}\} = f_{size}\{w_{ref}, h_{ref}\} = f_{ratio}\{w_{ref}, h_{ref}\}$$

To combine the factors of all three cases to one total K, all but one factor are normalized to the value of $K_{ref}$. Therefore K is calculated as:

$$K = f_{total}\{k, w, h\} = K_k \cdot \frac{K_{size}}{K_{ref}} \cdot \frac{K_{ratio}}{K_{ref}}$$

Figure 9:
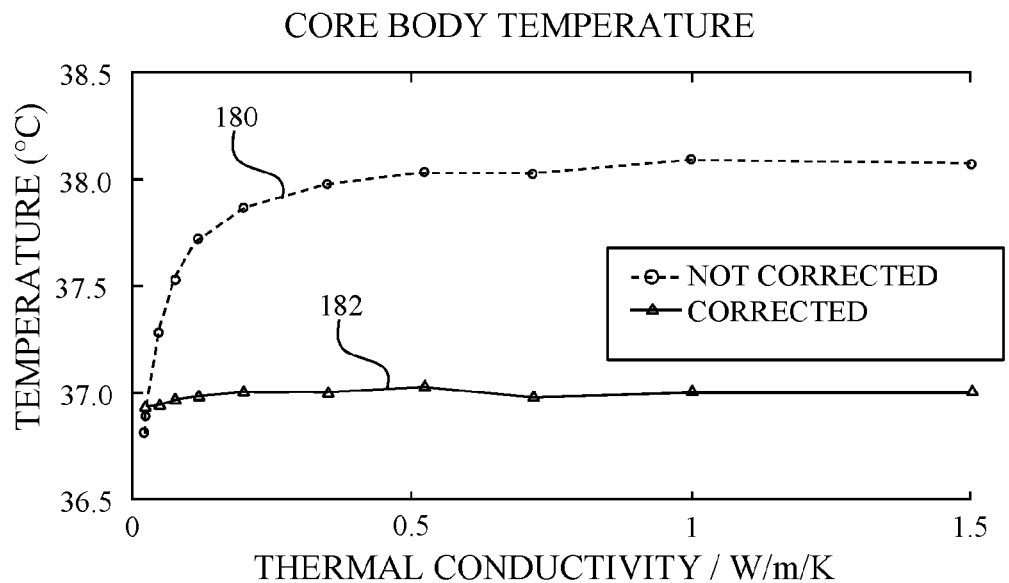
FIG. 9 depicts the results of simulations wherein sensor assemblies with different thermal conductivities were used to measure the heat flux through the sensor assemblies and a core body temperature was calculated with and without a determined correcting factor.

Once the correcting factor (K) was determined, the determined value/function was used in determining body core temperature for a number of simulations. FIG. 9 depicts the results of simulations wherein sensor assemblies with different thermal conductivities were used to measure the heat flux through the sensor assemblies and those values were used in calculating a core body temperature using the equation:

$$T_C = \frac{\dot{Q}''}{h_S} + T_S$$

The value for core body temperature obtained using this equation for an actual core body temperature of 37 degrees C. is shown by line 180.

A core body temperature was also calculated, for the same sensor assemblies, using a correcting factor (K) determined similarly to the example above. The determined correcting factor (K) was applied as follows:

$$\dot{Q}''_{skin} = \frac{\dot{Q}''_{sensor}}{K\{k, w, h\}}$$

The calculated core body temperatures for the same actual core body temperature of 37 degrees C. are shown by the line 182.

As is evident from FIG. 9, the incorporation of the determined correcting factor (K) eliminates a significant amount of the error generated by using only the heat flux through the sensor assembly with no correcting factor. Moreover, the calculation incorporating the correcting factor (K) consistently provides an accurate core body determination.

Figure 10:
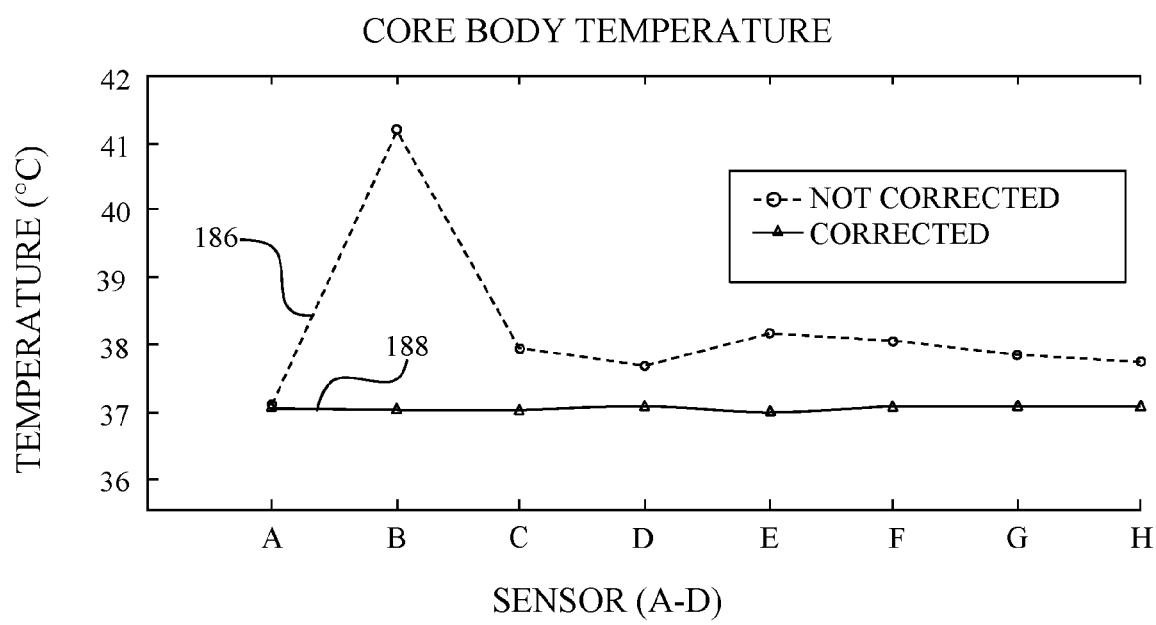
FIG. 10 depicts the results of simulations wherein sensor assemblies with different sizes were used to measure the heat flux through the sensor assemblies and a core body temperature was calculated with and without a determined correcting factor.

FIG. 10 depicts the results of simulations wherein sensor assemblies with different widths and heights were used to measure the heat flux through the sensor assemblies. The widths and heights for the sensor assemblies are shown in the following table:

| SENSOR | WIDTH | HEIGHT |
|---|---|---|
| A | 50 mm | 1 mm |
| B | 1 mm | 1 mm |
| C | 10 mm | 2 mm |
| D | 20 mm | 4 mm |
| E | 2.5 mm | 0.5 mm |
| F | 7.5 mm | 1.5 mm |
| G | 13 mm | 2.6 mm |
| H | 17 mm | 3.4 mm |

The values from the above table were used in calculating a core body temperature using the equation:

$$T_C = \frac{\dot{Q}''}{h_S} + T_S$$

The heat flux used in this calculation is the heat flux through the sensor assembly. The calculated core body temperature for an actual core body temperature of 37 degrees C. is shown by line 186.

A core body temperature was also calculated, for the same sensor assemblies, using a correcting factor (K) determined similarly to the example above. The determined correcting factor (K) was applied as follows:

$$\dot{Q}''_{skin} = \frac{\dot{Q}''_{sensor}}{K\{k, w, h\}}$$

The calculated core body temperatures for the same actual core body temperature of 37 degrees C. are shown by the line 188.

As is evident from FIG. 10, the incorporation of the determined correcting factor (K) eliminates a significant amount of the error generated by using only the heat flux through the sensor assembly with no correcting factor. Moreover, the calculation incorporating the correcting factor (K) consistently provides an accurate core body determination.

It should be noted that the particular simulation used will introduce or mask errors compared to an experiment using actual devices. For example, the heat flux or heat transfer rate of a body can typically only be read out at boundaries in a simulation. Therefore, for the purpose of the simulations above the heat flux for the sensor was read out at the lower surface of the sensor assembly and the sensor assembly was simulated with a uniform thermal conductivity. In contrast, a standard heat flux sensor assembly while typically exhibiting a higher thermal conductivity in a vertical direction (perpendicular to the sensor assembly surface) than in lateral direction still has losses in the lateral direction which ameliorate some of the increased heat flow caused by the sensor assembly. Accordingly, the simulation may overstate the errors in the calculation which do not incorporate the correcting factor (K). Nonetheless, FIGS. 9 and 10 demonstrate that the calculation of the core body temperature of a creature or body is significantly improved by using a correcting factor (K).

Figure 11:
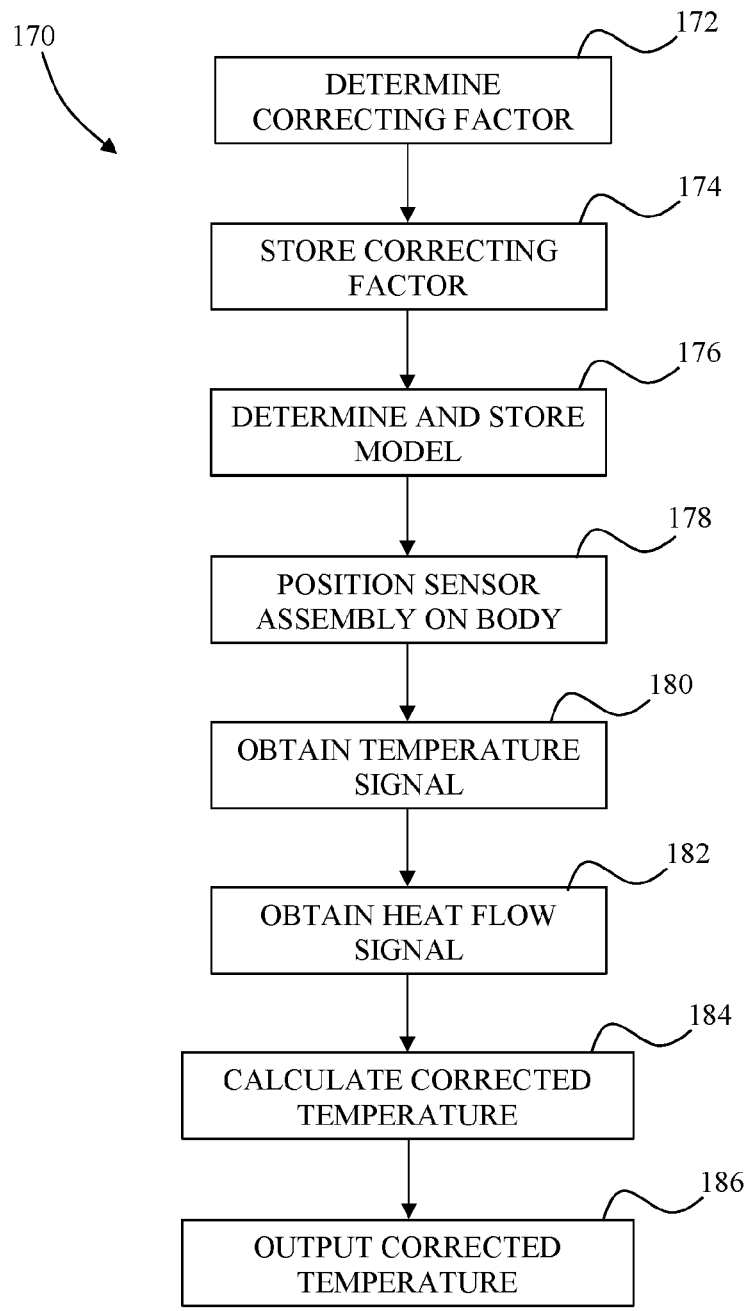
FIG. 11 depicts a process which is used in some embodiments to determine a correcting factor and apply the correcting factor when calculating a corrected temperature of a body.

FIG. 11 depicts a method 170 of operation of the system 100. At block 172, the correcting factor for a particular temperature sensing system is determined. As discussed above, the correcting factor optimally accounts for thermal conductivity of the sensor, a size of the sensor, and an aspect ratio of the sensor. While the correcting factor in some embodiments is determined by fully analyzing each of the above factors, in other embodiments a simplified analysis is performed. By way of example, the two dimensional approach described above provides for a reduction in the error of the corrected temperature. The determined correcting factor for a particular model is then stored at block 174.

At block 176 the remaining model for the temperature sensing system is stored in a desired memory. As discussed above, the model is directed to specific applications. For example, the thermal resistance for the "skin" for a particular body to be measured varies between applications. The thermal resistances, however, are readily determined based upon known or easily obtained material characteristics. Thus, while the thermal resistance of human skin is significantly different from the "skin" of a whale, which would include the blubber, and both are different from a "skin" of a tank or pipe, the values are nonetheless easily obtained.

As used herein, the "skin" or "outer skin" of a body means all substances through which heat flows from the core of the body to the sensor assembly. Thus, when the sensor is placed upon a piece of clothing, the clothing is considered to be part of the "outer skin" and thermal resistance of the clothing is preferably accounted for. The thermal resistance of the "outer skin" in some embodiments is uniquely established for each body. In other embodiments, the thermal resistance is selected based upon a nominal value ascribed to a group of similar bodies. In some embodiments, the thermal resistance of the skin is not incorporated, e.g., wherein surface temperature is to be determined.

At block 178 the sensor assembly is positioned on the body. Upon activation, the control unit for the system obtains a temperature signal (block 180) and a heat flow signal (block 182). The control unit then calculates a corrected temperature (block 184) using the model stored at block 176 including the correcting factor stored at block 174. The control unit then outputs the calculated corrected temperature (block 186) such as by causing the temperature to be displayed either on a display or other output device local to the sensor assembly, or at a remote output device. In some embodiments, the output is directed to a memory where it is stored pending a future transfer of the data.

Accordingly, the incorporation of the correcting factor (K) in a calculated core body temperature corrects for the thermal conductivity, height and width of the used sensor. While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

The invention claimed is:

1. A temperature sensor system comprising:
a housing;
a sensor assembly including (i) a temperature sensing portion configured to generate a first signal based upon a temperature of a body proximate a surface portion of the temperature sensing portion, and (ii) a thermoelectric generator portion configured to receive heat flow from the body through the temperature sensing portion and to generate a second signal based upon the heat flow;

a memory including program instructions and at least one correcting factor (K) stored therein; and a control unit operably connected to the sensor assembly and the memory, the control unit configured to execute the program instructions to obtain the first signal, obtain the second signal, obtain the at least one correction factor (K), calculate a corrected temperature ($T_c$) based upon the obtained first signal, the obtained second signal, and the obtained at least one correcting factor (K), and output the calculated corrected temperature, wherein:

the at least one correcting factor (K) is determined based upon at least one of a thermal conductivity of the sensor assembly, a size of the sensor assembly, and an aspect ratio of the sensor assembly;

the sensor assembly and control unit are housed by the housing;

the housing is configured to expose the sensor assembly to the body through a first side of the housing;

the housing includes a window on a side of the housing opposite the first side, the window configured to transfer the heat flow received by the thermoelectric generator portion out of the temperature sensor system; and the thermoelectric generator portion substantially surrounds the temperature sensing portion except at the surface portion.

2. The temperature sensor system of claim 1, wherein the body includes an outer skin and the control unit is configured to calculate the corrected temperature based upon the following equation:

$$\dot{Q}''_{skin} = \frac{\dot{Q}''_{sensor}}{K}$$

wherein $\dot{Q}''_{skin}$ is heat flux through the outer skin, and $\dot{Q}''_{sensor}$ is heat flux through the sensor assembly.

3. The temperature sensor system of claim 2, wherein the at least one correcting factor (K) is determined based upon the thermal conductivity of the sensor assembly, the size of the sensor assembly, and the aspect ratio of the sensor assembly.

4. The temperature sensor system of claim 1, further comprising:

a display, wherein the control unit is operably connected to the display and configured to execute the program instructions to display the calculated corrected temperature with the display.

5. The temperature system of claim 1, wherein the control unit is further configured to execute the program instructions to calculate the corrected temperature (Tc) based upon a thermal resistance of an outer skin of the body.

6. A method of providing a corrected temperature, comprising:

exposing a sensor assembly to the body through a first side of a housing;

transferring a heat flow, received by a thermoelectric generator portion of the sensor assembly from the body through a temperature sensing portion of the sensor assembly, out of the sensor assembly through a window on a side of the housing opposite the first side;

obtaining, using a control unit executing program instruction stored in a memory, a first signal from the temperature sensing portion of the sensor assembly, the first signal based upon a temperature of the body proximate a surface portion of the temperature sensing portion;

obtaining, using the control unit, a second signal from the thermoelectric generator portion of the sensor assembly, the second signal based upon the heat flow received by the thermoelectric generator portion from the body through the temperature sensing portion; and calculating, with the control unit, the corrected temperature (Tc) based upon the obtained first signal, the obtained second signal, and at least one correcting factor (K) stored in the memory, the at least one correcting factor (K) determined based upon at least one of a thermal conductivity of the sensor assembly, a size of the sensor assembly, and an aspect ratio of the sensor assembly, wherein the control unit and sensor assembly are housed by the housing; and the thermoelectric generator portion substantially surrounds the temperature sensing portion except at the surface portion.

7. The method of claim 6, wherein the calculating, with the control unit, a corrected temperature (Tc) comprises:

calculating, with the control unit, the corrected temperature (Tc) based upon the following equation:

$$\dot{Q}''_{skin} = \frac{\dot{Q}''_{sensor}}{K}$$

wherein $\dot{Q}''_{skin}$ is heat flux through an outer skin of the body, and $\dot{Q}''_{sensor}$ is heat flux through the sensor assembly.

8. The method of claim 7, further comprising:

determining the at least one correcting factor (K) based upon the thermal conductivity of the sensor assembly, the size of the sensor assembly, and the aspect ratio of the sensor assembly.

9. The method of claim 6, further comprising:

displaying, under control of the control unit, the calculated corrected temperature on a display.

10. The method of claim 6, wherein the calculating, with the control unit, the corrected temperature (Tc) comprises:

calculating the corrected temperature (Tc) based upon a thermal resistance of an outer skin of the body.

* * * * *